United States Patent [19]

Kang

[11] Patent Number: 5,098,709

[45] Date of Patent: Mar. 24, 1992

[54] METHOD OF ADMINISTRATING A FUSED SALT FROM NATURAL SUBSTANCES, NAMELY GINKGO, PERSIMMON, PINE, AND BAMBOO IN THE TREATMENT OF INFLAMMATIONS

[76] Inventor: Kwon J. Kang, 101-5 Nonhyun-Dong, Kangnam-Ku, Seoul, Rep. of Korea

[21] Appl. No.: 442,600

[22] Filed: Nov. 29, 1989

Related U.S. Application Data

[63] Continuation of Ser. No. 143,397, Jan. 13, 1988, Pat. No. 4,915,946.

[51] Int. Cl.$^5$ .............................................. A61K 35/78
[52] U.S. Cl. ............................ 424/196.1; 424/195.1; 514/783; 426/648; 426/806
[58] Field of Search ................... 426/648, 806; 424/195.1, 196.1; 514/783

[56] References Cited

U.S. PATENT DOCUMENTS

| 2,689,794 | 9/1954 | Jackson | 426/648 |
| 4,683,140 | 7/1987 | Kang | 426/597 |
| 4,915,946 | 4/1990 | Kang | 424/195.1 |

*Primary Examiner*—John W. Rollins
*Assistant Examiner*—Ralph Gitomer
*Attorney, Agent, or Firm*—Birch, Stewart, Kolasch & Birch

[57] ABSTRACT

A method of treating inflammation in a mammalian recipient by administrating to the mammalian recipient an effective amount of a fused salt from natural substances, namely Ginkgo, Persimmon, Pine, and Bamboo for the treatment of inflammations.

4 Claims, 4 Drawing Sheets

METHOD OF ADMINISTRATING A FUSED SALT FROM NATURAL SUBSTANCES, NAMELY GINKGO, PERSIMMON, PINE, AND BAMBOO IN THE TREATMENT OF INFLAMMATIONS

CROSS-REFERENCE TO RELATED APPLICATION

This is a continuation application of the U.S. patent application, Ser. No. 07/143,397, filed Jan. 13, 1988, which is now allowed.

BACKGROUND OF THE INVENTION

1. Field of the Invention

The present invention relates to a method of administrating a fused salt from natural substances, namely sea salt, Ginkgo, Persimmon, Pine, and Bamboo in treating inflammations. More particularly, the present invention relates to an evaporated salt composition utilizing ash from sea salt and leaves obtained from a combination of Ginkgo, Persimmon, Pine, and Bamboo in the treatment of inflammations such as acute or chronic bronchitis, vaginitis, chronic bronchial asthma, vicious dermatitis, leucorrhea, or the like. Still further, the present invention pertains to a method of administrating of 0.05 g to 0.5 g/Kg per day, preferably 0.07 to 0.03 g/Kg per day of ash from sea salt, which is a very coarse-grained variety of common salt originally obtained from sea water, and the leaves of *Ginkgo biloba L.*, *Diospyros Kalsi L.*, *Pirus monophylla*, and *Bambusa arundinacea* to a human in treating inflammations.

2. Description of the Prior Art

There are many types of known sodium chloride salts such as fine granulated salt, table salt, evaporated salt, iodized salt and the like for seasoning or preserving food. Also, there are many types of known tea made from natural substances such as persimmon and pine leaves. In the present inventor's related U.S. patent application Ser. No. 07/143,397 filed Jan. 13, 1988, now allowed, an evaporated salt is disclosed which is made of ash from sea salt and leaves of Ginkgo, Persimmon, Pine and Bamboo. However, such evaporated salt is unknown to treat inflammations by administrating of 0.05 g to 0.5 g/Kg per day thereof to human.

SUMMARY OF THE INVENTION

Accordingly, it is an object of the present invention to provide a method of administrating of 0.05 g to 0.5 g/Kg per day of an evaporated salt from sea salt, and leaves of Ginkgo, Persimmon, Pine and bamboo to a patient for treating inflammations.

Another object of the present invention is to provide an evaporated salt composition utilizing ash made from sea salt, and leaves of Ginkgo, Persimmon, Pine, and bamboo for use in adding to foods, food additives, soup, soft drink, vitamins, conventional remedy forms, or the like so as to treat inflammations.

A further object of the present invention is to provide an inflammatory remedy containing ash formed from sea salt and leaves of Ginkgo, Persimmon, Pine and Bamboo at temperatures of about 1,000° to 1,300° C.

Other objects and further scope of applicability of the present invention will become apparent from the detailed description given hereinafter. It should be understood, however, that the detailed description and specific examples, while indicating preferred embodiments of the invention, are given by way of illustration only, since various changes and modifications within the spirit and scope of the invention will become apparent to those skilled in the art from this detailed description.

In carrying out the present invention, Ginkgo, Persimmon, Pine and Bamboo are used to form an initial mixture with sea salt in a ratio of about 200:1 by weight percent. The mixture is placed in a special furnace, and then burned by using firewood of Ginkgo, Persimmon, Pine and Bamboo at a temperature of about 1,000° to 1,300° C. to produce a solid salt ash. The solid salt ash is then repeatedly burned about 5 to 6 times in accordance with the above method to produce a burned solid salt ash. This burned solid salt ash is then put into a Bamboo tube and further burned with firewood of Ginkgo, Persimmon, Pine and Bamboo at about 1,000° to 1,300° C. Finally, the burned solid salt ash is put into an electric furnace, and heated at a temperature, of about 1,300° C. to manufacture the salt composition of the present invention. The obtained fused salt is administrated at a dosage of from 0.05 g to 0.5 g/Kg per day to a patient, such as a human, for treating inflammations.

BRIEF DESCRIPTION OF THE DRAWINGS

The present invention will become more fully understood form the detailed description given hereinbelow and the accompanying drawings which are given by way of illustration only, and thus are not limitative of the present invention, and wherein.

DETAILED DESCRIPTION OF THE INVENTION

Referring now in detail to the preferred embodiments of the present invention and to the drawings for the purpose of illustrating preferred embodiments of the present invention, there is provided by the present invention a remedial salt composition for use in a medicinal food. The medicinal food salt composition of the present invention is made from natural substances, namely sea salt, Ginkgo, Persimmon, Pine and bamboo.

Figure 1:
FIG. 1 is an enlarged picture of prior art sea salt.
Figure 2:
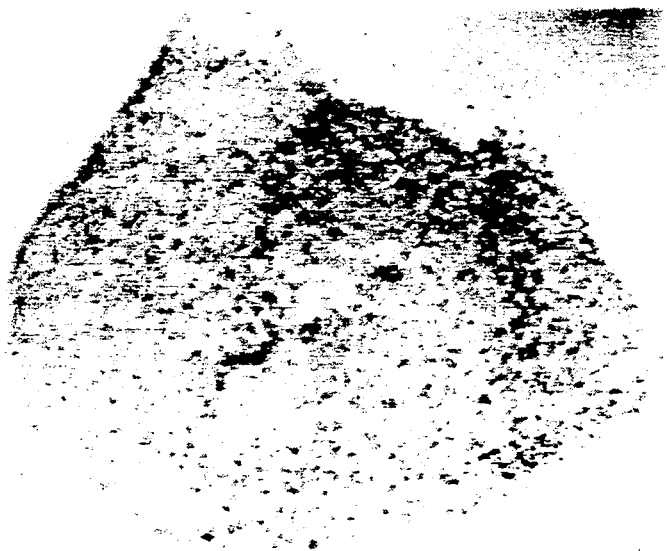
FIG. 2 is an enlarged picture of an ash-salt obtained from the third step of the present invention.
Figure 3:
FIG. 3 is an enlarged picture of a solid salt obtained from the fourth step of the present invention.
Figure 4:
FIG. 4 is an enlarged picture of a solid salt obtained from the fifth step of the present invention.
Figure 5:
FIG. 5 is enlarged pictures of solved salt of the prior art sea salt at temperature of 900°-1,000° C. (left side) when compared with the salt of the present invention which is fused at a temperature of 400°-600° C. of the present invention.
Figure 6:
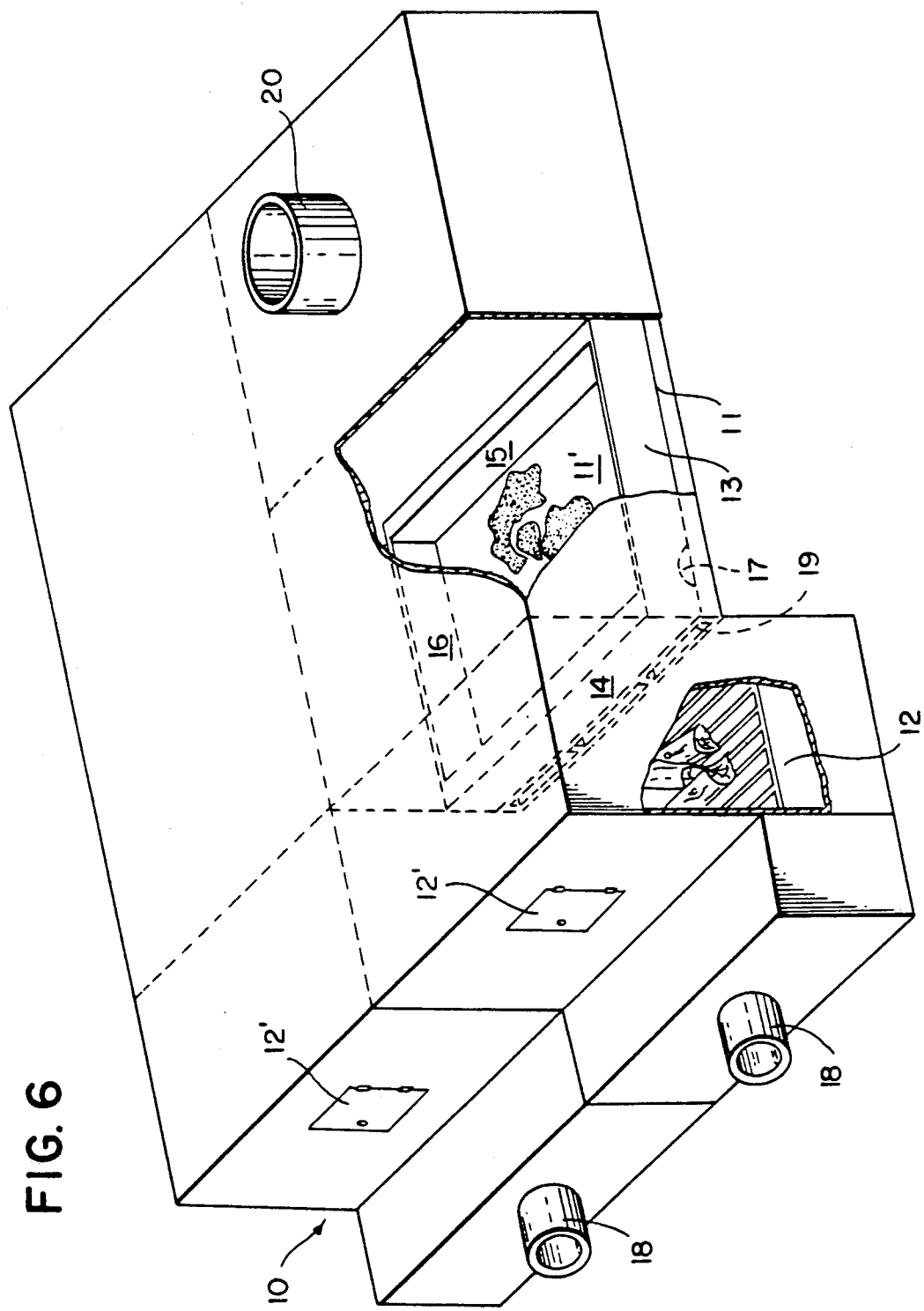
FIG. 6 is a perspective view of a furnace of the present invention.

Initially, untreated seal salt as shown in FIG. 1 is heated in a combustion container 11 disposed in a furnace 10 as shown in FIG. 6 at a temperature of about 400° to 600° C. to produce an evaporated salt powder. During this heating, the three doors 14, 15, and 16 are closed. This evaporated powder salt is then combined with leaves from natural substances to form an initial mixture. The leaves are prepared by cutting a quantity of dry leaves from the Ginkgo, Persimmon, Pine and Bamboo families to at a size of about 200 mesh. The Ginkgo, Persimmon, Pine and Bamboo leaves are combined in equal amounts by weight, with respect to each other. The quantity of the evaporated salt powder to be combined with the leaves from the genus Ginkgo, Persimmon, Pine and bamboo used is in an amount of about 95% of salt as compared to 5% by weight of leaves. In one preferred embodiment, 10 kg of sea salt in the form of the evaporated salt powder and 500 g of the leaves from natural substances are combined in an initial mixture.

In a second step, as shown in FIG. 6, the initial mixture is put into the furnace 10. That is, the initial mixture is placed in a combustion container 11 having air inlets 18 and firewood from Ginkgo, Persimmon, Pine and bamboo wood is placed in a fireplace 12 having doors 12'. The combustion container 11 comprises a panel 11' disposed at the bottom thereof, front, rear and left side doors 14, 15, and 16, and a solution outlet 17 disposed at the bottom of a right side wall 13. At this time, the front and rear doors 14 and 15 are closed and the left side door 16 is opened. When the firewood is burned using fresh air through the air inlets 18, the fire passes through a fire tunnel 19 to a chimney 20. At this time, the temperature in the initial mixture may be measured about 1,000° to 1,300° C. and natural minerals such as sulfur, potassium, or the like from the firewood are combined with the initial mixture so that most of the fusing solution is discharged through the solution outlet 17 and little fusing solution is evaporated away through the chimney 20. The fusing solution from the solution outlet 17 is immediately solidified to obtain a black fused salt.

In a third step, the black fused solid is pulverized in a conventional pulverizer to obtain a powder therefrom. The same quantity of untreated dry leaves as used in the initial first step described above is then added to the pulverized powder. The combustion procedure of the above-described second step of the present invention is then repeated. The present third step is then repeated about 5 to 6 times to obtain a pulverized final product containing a large quantity of minerals therein.

Figure 7:
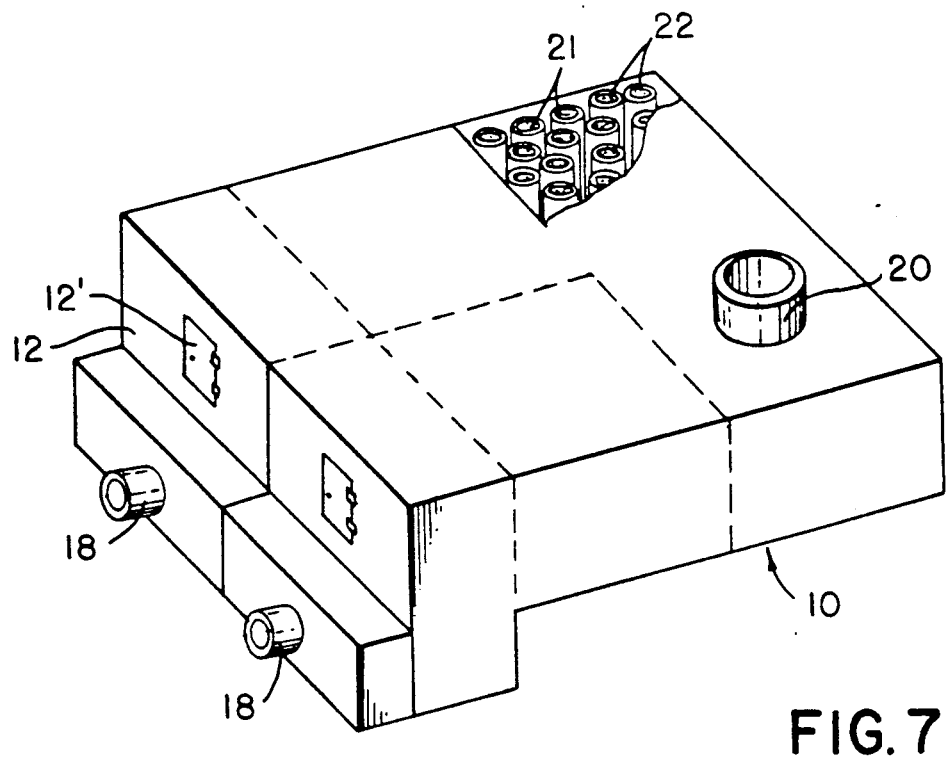
FIG. 7 is a perspective view of a furnace containing a plurality of Bamboo tubes with the evaporated salt of the present invention.
Figure 8:
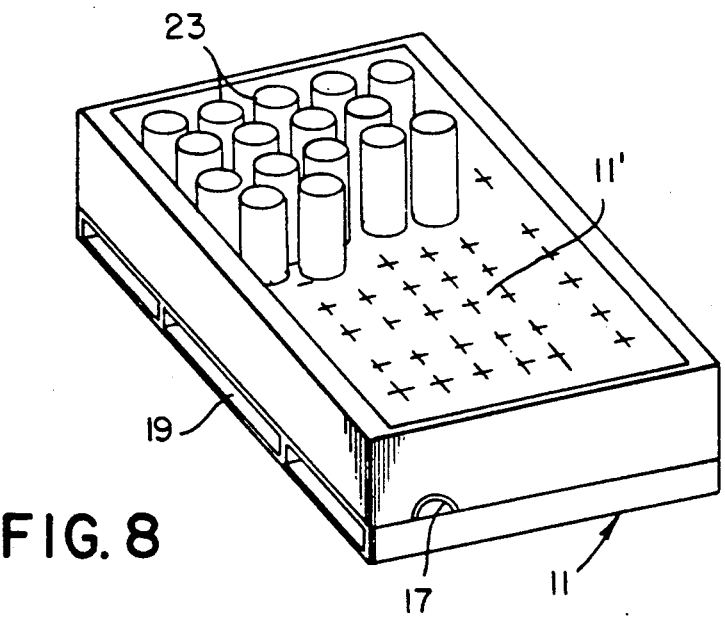
FIG. 8 is a perspective view of a panel containing a plurality of solid salt rods.

In a fourth step, the pulverized powder 22 from the third step is put into a plurality of bamboo wood tubes 21 and the plurality of bamboo wood tubes 21 are stood on end in the combustion container 11 which is placed in the furnace 10 as shown in FIG. 7. At this time, firewood from Ginkgo, Persimmon, Pine and Bamboo is utilized as a solid fuel for burning the bamboo wood tubes which contain the pulverized powder rod. This process results in forming a solid salt rod 23 in the combustion container 11 of the furnace 10 as shown in FIG. 8.

In a fifth step, the plurality of solid salt rods 22 are put into the combustion container 11 in the furnace 10 and heated with the firewood at a temperature of about 1,000° to 1,300° C. for fusion and discharged through the solution outlet 17. The fusing solution becomes a black fused solid product in the atmosphere.

In a sixth step, the black fused solid produce is placed in an electric furnace and heated to a temperature of about 400° to 600° C. at which point the final fusing begins. Thereafter, the temperature increases until about 1,300° C. and impurities contained in the solid product are completely combusted thereby purifying the product. Conventional untreated sea salt normally starts to fuse at a much higher temperature of about 900° C. when compared with that of the product of the present invention. This indicates a difference in properties between the product of the present invention and conventional untreated sea salt.

The present invention includes a composition for use as a treating agent for inflammations, the composition comprising the obtained fused salt with an amount thereof in foods such as soup, milk, juice, salad, or the like, food additives, soft drinks, vitamins, and drug preparation forms such as tablets, capsules, ointments, liquids, syrups, suppositories, powders, and the like.

The present invention also includes a method of treating inflammations such as acute or chronic bronchitis, vaginitis, chronic bronchial asthma, vicious dermatitis, leucorrhea, or the like in a mammalian recipient by administrating to the mammalian recipient about 0.05 g to 0.5 g/Kg per day, preferably 0.07 to 0.3 g/Kg per day of the free fused salt, a drug composition or a food composition thereof.

In order for the fused salt to have maximum effectiveness in treating inflammations, the fused salt should be ingested orally about 4–6 times a day, preferably 4 times between meals.

The composition in a tablet composition preferably contains 0.5 g to 1.5 g of the fused salt therein, more preferably 1 g of the fused salt.

When the composition is in the form of a vitamin tablet it will generally contain 1 g to 3 g of the fused salt therein, more preferably 2 g of the fused salt, the remainder being essentially vitamins and a binder for the vitamins.

When the composition is in the form of a powder or an ointment, the powder or ointment will generally contain 1 g to 3 g of the fused salt therein, more preferably 2 g of the fused salt for treating burns, scald dermatophytosis, eczema, or the like.

The present invention will now be described in more detail in connection with the following examples which should be considered as being exemplary and not limitative of the present invention.

Test Example 1: Treatment of Bronchitis

K.C.S. is a 62 year old woman weighing 56 Kg diagnosed as holding chronic bronchitis and asthma. For more than twenty years, she has been suffering from severe cough and phlegm to constant hard breathing and frequently causing depression of her breast with rising blood pressure after long continuous coughs. Such a condition becomes more serious when the seasons change. She was given a 60 day using the fused salt of the present invention treatment in two consecutive periods with an interval of 15 days between them. During the first half of procedure, four tablets were given each day, each between the meals. Each tablet weighted 1 g (0.07 g/Kg body wt.).

Some nausea was observed during treatment, but not serious side effects. After a 15 day interval passed, the second half of the procedure commenced, when 6 tablets were given each day, each weighing 1 g (0.11 g/Kg. B.W.), in 6 turns. The tablet was to be melted slowly in the mouth.

The quantity of the medicine was increased compared to that of the first half, but no more nausea was experienced and no disease symtomized by thirst was detected. It was noted that phlegm and cough was considerably calmed after the first half of the procedure though a little depressed feeling on the breast remained, which was vanished perfectly after the second half.

It was reported that no signs of toxicity concerning the nerve were discovered and the patient is now in the condition that she is not showing any signs of chronic bronchitis or asthma even upon the change of the seasons.

Her usual blood pressure of 110-90 mmHg showed no change after the first half of the procedure, while it showed 130-90 mmHg with some rise during the second half of the procedure. It, however, is not above normal human blood pressure.

Several other patients with similar chronic bronchitis and asthma were also given similar treatment. All of them proved the effect of the treatment, though each was treated in a slightly different way by varying the period and quantity of medicinal treatment. In case of inherited confined bronchus it was discovered that the treatment did not prove effective in ultimately expanding the bronchus itself, though it was observed that the amount of phlegm was reduced, and this factor as an obstacle to breathing was relieved more or less.

Test Example 2: Vicious dermatitis

Jeong J. I. is a 24 year old male college student weighing 73 Kg, who was diagnosed as having vicious dermatitis at the National Police Hospital in October, 1987. He then was serving as a member of the Street Police of the Combat Police of the Republic of Korea. After that, he was treated with internal and external remedies at a dermatology department in a private hospital for a year or so.

The treatment was not sufficiently effective. Whenever medicine is suspended it would erupt rapidly and spread all over the body with minor illness. He had to visit many dermatology hospitals and finally visited a leprosarium, the final step in dermatological treatment.

Yet no improvement was shown. Furthermore, because of using medicine habitually, a sour, heavy stomach and even dizziness was experienced by him. He took a 14 day course GARAM treatment. For the first three days, he took three tablets a day, each weighing 1 g (0.04 g/Kg body wt.) and 22.5% GARAM liquid (5 pills melted in 20 ml of distilled water) through cotton on the erupted area.

As a consequence of this treatment, it was reported that the patient came to feel relief of his minor illness and the spreading and erupting thereof completely vanished. Moreover, gastritis from the long period of internal administration was overcome and any recurrence thereof or side effect therefrom was not observed. He has been living a sound and ordinary life so far. Also, a change in blood pressure (130-80 mmHg) was not observed during the short period of GARAM treatment.

Beside this, several dermatophytosis patients were treated by a similar method of treatment. The efficacy of the above treatment was proven over varying periods and quantities of dosages. Yet some small side effects and burns appeared.

Test Example 3: Of Female Chill, Leucorrhea and Vaginitis

Shin S. Y. is a 66 year old woman weighing 50 Kg, who had failed in recovering from various leucorrhea and vaginitis until she took GARAM treatment in 1987. By the time she went into GARAM treatment, she had been wearing pads against secretion continuously running down with a stench and feeling something chilly and heavy hanging on the lower part of her abdomen.

Furthermore, occasionally light-red blood was found mixed with the secretion. These physical conditions lasted for fifteen years and severe gastritis from frequent use of antibiotic medicine during the period was also experienced. She took GARAM treatment for twenty one days, while internal administration and GARAM vaginal pills were given simultaneously.

During the first week of the period, five GARAM pills, each weighing 1 g (0.1 g/Kg body wt.) were given simultaneously with 6 GARAM vaginal pills in such a method as putting them into the vagina. During the second week, eight GARAM pills, each weighing 1 g (0.16 g/Kg B.W.), three added, were given and the vaginal pill four times a day. During the last week, four GARAM pills, each weighing 1 g (0.8 g/Kg B.W.), were given decreased, and the vaginal pill twice a day, morning and night.

As a consequence of this treatment, the patient excreted more secretion and the stench increased. But in several days the stench and the secretion began to decrease and in the third week the disorder was significantly relieved to such a degree as at a normal state and her stomach was also reported as recovering well. Now no toxicity is detected throughout her body and she is completely sound and living as normal a life as any other woman's.

Patients suffering similar conditions also recovered through the application of the same amount of fused salt vaginal pills between four times and six times a day for nine to ten days. As a consequence, it was possible to attain a maximum effect through treatment similar to other antibiotic medicines. However, it must be reported that leucorrhea from gonorrhea or urethra did not heal. As to the reason why the fused salt of the invention is effective for female leucorrhea and vaginal aversion and makes it possible to heal leucorrhea when used, the following theory is suggested. When the fused salt is inserted into the vagina, with a large amount of secretion, it works to absorb certain substances. With this procedure, the fused salt works to heal and refresh the treated inflammation.

The treatment of the invention has also proved effective to constipated patents. The procedure included inserting a salt pill somewhat deep into the anus, which enabled the evacuation to proceed smoothly in two minutes or three. It is required that the patient holding cold leucorrhea and inflamed vagina, when treated after insertion, must use a pad. In inserting salt into the anus, it is recommended to be carried out using jelly.

Formulation Example 1: Tablet

The final purified product resulting from the above-described process is manufactured as a tablet, wherein each tablet contains about 1 g of the purified product. This tablet is useful for treating inflammatory disease in the mouth such as caries, gumboil, tonsillitis, asthma, and the like.

Formulation Example 2: Solution 1 g of the final purified product is dissolved in 100 ml of sterile distilled water and is filtered to obtain filtrate for use in eye, nose and ear diseases. The solution can also be utilized as a mouthwash.

Formulation Example 3: Ointment

The purified product is mixed with a conventional ointment base to cure dermatitis, eczema, athlete's foot and hemorrhoids.

Table I shows an analysis of the elements in the final purified product of the present invention when compared with a conventional bay salt disclosed by the prior art as follows:

TABLE I

|     | A fused salt produced by the present invention | A conventional sea salt |
|-----|-----|-----|
| NaCl | 96% | 99.84% |
| Ca | 0.16% | 0.03% |
| Mg | 0.56% | 0.006% |
| S | 0.88% | 0.074% |
| Fe | 130 ppm | 0.5 ppm |
| Cu | 5 ppm | 0.14 ppm |
| Na | 37.2% | 39.2% |
| Cl | 58.8% | 60.6% |

As shown in Table I, the fused salt according to the present invention which was analyzed was acquired at the Korea Advanced Institute of Science and Technology, Seoul, Korea.

The invention being thus described, it will be obvious that the same may be varied in many ways. Such variations are not to be regarded as a departure from the spirit and scope of the invention, and all such modifications as would be obvious to one skilled in the art are intended to be included in the scope of the following claims.

What is claimed is:

1. An antiinflammatory pharmaceutical composition for treating inflammation in a mammalian recipient in need thereof which comprises an effective antiinflammatory amount of a fused salt and a pharmaceutically acceptable carrier therefor, said fused salt having been prepared by a process which comprises the steps of:
   (a) heating a predetermined quantity of salt at an elevated temperature to form a salt powder;
   (b) combining said salt powder with leaves from the genus Ginkgo, Persimmon, Pine and Bamboo to form an initial mixture, said salt powder and said leaves being present in amount of about 95% and 5% by weight, respectively;
   (c) combusting said initial mixture in a furnace using firewood at a temperature of about 1,000° to 1,300° C. to produce a first fusing solution which is solidified into a first fused solid;
   (d) pulverizing said fused solid to form a pulverized solid;
   (e) combusting a mixture formed from combining said pulverized solid with leaves from the genus Ginkgo, Persimmon, Pine and Bamboo in said furnace with firewood at a temperature of about 1,000° to 1,300° C. to produce a second fused solid;
   (f) repeating steps (d) and (e) at least 5 times;
   (g) combusting a plurality of Bamboo tubes which contain said fused solid produced by step (f) in said furnace to produce solid salt rods;
   (h) heating said solid salt rods in said furnace at a temperature of about 1,000° to 1,300° C. to produce a third fusing solution which is solidified into a third fused solid; and
   (i) heating said third fused solid in an electronic furnace to a temperature of about 1,300° C. to form a final fused salt composition.

2. A method for treating inflammation in a mammalian recipient in need thereof which comprises administering about 0.05 to 0.5 g/Kg per day of a fused salt to said recipient, said fused salt containing salt powder combined with leaves from the genus Ginkgo, Persimmon, Pine and Bamboo, said salt powder and said leaves being present in amounts of about 95% and 5% by weight, respectively.

3. The method of claim 2, wherein about 0.07 to 0.3 g/Kg per day of said fused salt is administered to said mammalian recipient.

4. The method of claim 2, wherein the inflammations are cough and inflammation of the trachea, tooth-ache and scaling, leucorrhea, eczema, and epidemic conjunctivitis.

* * * * *